US005693659A

United States Patent [19]
Head et al.

[11] Patent Number: 5,693,659
[45] Date of Patent: Dec. 2, 1997

[54] SUBSTITUTED OXIME DERIVATIVES AND PROCESSES FOR THEIR PREPARATION

[75] Inventors: John Clifford Head, Windsor; Graham John Warrellow, Northwood; Rikki Peter Alexander, High Wycombe, all of United Kingdom

[73] Assignee: Celltech Therapeutics Limited, Slough, United Kingdom

[21] Appl. No.: 493,649

[22] Filed: Jun. 22, 1995

[30] Foreign Application Priority Data

Jun. 23, 1994 [GB] United Kingdom ............... 9412672

[51] Int. Cl.$^6$ ............................................. A61K 31/44
[52] U.S. Cl. ............................................. 514/357; 546/333
[58] Field of Search ........................... 546/333; 514/357

[56] References Cited

U.S. PATENT DOCUMENTS

| | | | |
|---|---|---|---|
| 4,012,495 | 3/1977 | Schmeichen et al. | 424/274 |
| 4,015,017 | 3/1977 | Gazave | 424/331 |
| 4,153,713 | 5/1979 | Huth et al. | 424/274 |
| 4,193,926 | 3/1980 | Schmiechen et al. | 260/326.5 |
| 4,303,649 | 12/1981 | Jones | 424/177 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,550,137 | 8/1996 | Beeley et al. | 514/354 |
| 5,580,888 | 12/1996 | Warrellow et al. | 514/332 |
| 5,608,070 | 3/1997 | Alexander et al. | 546/270 |

FOREIGN PATENT DOCUMENTS

| | | |
|---|---|---|
| 0 233 461 A2 | 8/1987 | European Pat. Off. |
| 0 295 210 A1 | 12/1988 | European Pat. Off. |
| 0 337 943 A2 | 10/1989 | European Pat. Off. |
| 0 393 500 A1 | 10/1990 | European Pat. Off. |
| 0 490 823 A1 | 6/1991 | European Pat. Off. |
| 0 470 805 A1 | 2/1992 | European Pat. Off. |
| 0497564A1 | 8/1992 | European Pat. Off. |
| 0 511 865 A1 | 11/1992 | European Pat. Off. |
| 0 537 742 A2 | 4/1993 | European Pat. Off. |
| 0 564 409 A1 | 10/1993 | European Pat. Off. |
| 250 1443 | 7/1975 | Germany. |
| 3-77872 | 4/1991 | Japan. |
| 3-77923 | 4/1991 | Japan. |
| 1588639 | 4/1981 | United Kingdom. |
| WO 87/06576 | 11/1987 | WIPO. |
| WO 91/15451 | 10/1991 | WIPO. |
| WO 91/16892 | 11/1991 | WIPO. |
| WO 92/00968 | 1/1992 | WIPO. |
| WO 92/06085 | 4/1992 | WIPO. |
| WO 92/06963 | 4/1992 | WIPO. |
| WO 92/07567 | 5/1992 | WIPO. |
| WO 92/12961 | 8/1992 | WIPO. |
| WO 92/19594 | 11/1992 | WIPO. |
| WO 92/19602 | 11/1992 | WIPO. |
| WO 93/19748 | 10/1993 | WIPO. |

(List continued on next page.)

OTHER PUBLICATIONS

Newton, A.C., "Protein Kinase C: Structure, Function, Regulation", *J. Biol. Chem.*, 1995, 270(48), 28495–28498.

(List continued on next page.)

*Primary Examiner*—Amelia Owens
*Attorney, Agent, or Firm*—Woodcock Washburn Kurtz Mackiewicz & Norris LLP

[57] ABSTRACT

Compounds of general formula (1) are described:

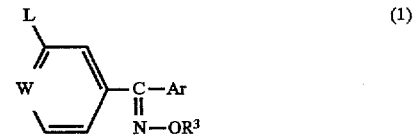

wherein ═W— is (1) ═C(Y)— where Y is a halogen atom, or an alkyl or —XR$^a$ group where X is —O—, —S(O)$_m$— [where m is zero or an integer of value 1 or 2], or —N(R$^b$)— [where R$^b$ is a hydrogen atom or an optionally substituted alkyl group] and R$^a$ is a hydrogen atom or an optionally substituted alkyl group or, (2) ═N—; L is a —XR, [where R is an optionally substituted alkyl, alkenyl, cycloalkyl or cyloalkenyl group], —C(R$^5$)═C(R$^1$)(R$^2$) or [—CH(R$^5$)]$_n$ CH(R$^1$)(R$^2$) group where R$^5$ is a hydrogen or a fluorine atom or a methyl group, and R$^1$ and R$^2$, which may be the same or different, is each a hydrogen or fluorine atom or an optionally substituted alkyl, alkenyl, alkynyl, alkoxy, alkylthio, —CO$_2$R$^6$, [where R$^6$ is a hydrogen atom or an optionally substituted alkyl, aralkyl, or aryl group], —CONR$^7$R$^8$ [where R$^7$ and R$^8$, which may be the same or different are as defined for R$^6$], —CSNR$^7$R$^8$, —CN or —NO$_2$ group, or R$^1$ and R$^2$ together with the C atom to which they are attached are linked to form an optionally substituted cycloalkyl or cycloalkenyl group and n is zero or the integer 1; Ar is a group —(CH$_2$)$_n$—Z—Ar' where Ar' is an optionally substituted monocyclic or bicyclic heteroaryl group and Z is a bond, an atom —O—, or —S— or a group —N(R$^b$)— and n is zero or the integer 1, 2, 3 or 4; R$^3$ is a hydrogen atom, or an optionally substituted alkyl, alkenyl, alkynyl, —C(O)R$^4$ (where R$^4$ is an amino, alkylamino, arylamino, alkoxy, aryloxy or an optionally substituted alkyl group) or —C(S)R$^4$ group; and the salts, solvates, hydrates, prodrugs and N-oxides thereof.

Compounds according to the invention are phosphodiesterase type IV inhibitors and are useful in the prophylaxis and treatment of disease such as asthma where an unwanted inflammatory response or muscular spasm is present.

18 Claims, No Drawings

FOREIGN PATENT DOCUMENTS

| | | |
|---|---|---|
| WO 94/02465 | 2/1994 | WIPO . |
| WO 94/12461 | 6/1994 | WIPO . |
| WO 94/14742 | 7/1994 | WIPO . |
| WO 94/20446 | 9/1994 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |

OTHER PUBLICATIONS

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Ashton, "Selective Type IV Phosphodieseterase Inhibitors as Antiasthmatic Agents. The Synthesese and Biological Activities of 3-(Cyclopentyloxy)-4-methoyoxybenzamides and Analogues", *J. Med. Chem.*, 1994, 37, 1696–1703.

Beavo & Reifsnyder, "Primary Sequence of Cyclic Nucleotide Phosphodiesterase Isozymes and the Design of Selective Inhibitors" *TIPS*, 1990, 11, 150–155.

Buu–Hoi, N.P. et al., "Bromination of Some 1,2,2-Triarylethylenes" *J. of Organic Chemistry*, 1958, 1261–1263.

Buu–Hoi et al., "New Method for the Synthesis of ω,ω-Diarylacetophenones Aminated in the Aromatic Nucleus. Plynitration of Triarylethylenes", *Chem. Abstr.*, 1964, 61(13), 16006h.

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Chemical Abstracts. Registry Handbook—Number Section. Printed Issues Columbus US *compounds with registry No. 95992-21-5; 95971-60-1; 90053-37-5; 82668-18-6; 80395-25-1; 49610-49-3.

Daves, G.D. et al., "Pyrimidines. XIII. 2–and 6–Substituted 4–Pyrimidinecarboxylic Acids", *J. Of Hev. Chem.*, 1964, 1, 130–133.

Dietl, F. et al., "Chinone von Benzo–und Dibenzokronenethern", *Synthesis*, 1985, 626–631.

El–Wakil et al., "Study of the proton magnetic resonance of methoxytamoxifen towards ortho–substituition", *Chem. Abstr.*, 1992, 116, 255248t.

Geissler, J.F. et al., "Thiazolidine–Diones. Biochemical and Biological Activity of a Novel Class of Tyrosine Protein Kinase Inhibitors", *J. Of Biol. Chem.*, 1990, 265(36), 22255–22261.

Hanks, S.K. et al., "The eukaryotic protein kinase superfamily: kinase (catalytic) domain structure and classification", *FASEB J.*, 1995, 9, 576–596.

Hirose et al., "Styrene Derivatives and Electrophotpgraphic Photoreceptor Containing Them", *Chem. Abstr.*, 1993, 118, 136183z.

Ishikura, M. et al., "An Efficient Synthesis of 3–Heteroarylpyridines via Diethyl–(3–pyridyl)–borane" *Synthesis*, 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2), 123–132.

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low-$K_m$3 Rolipram-sensitive Cyclic AMP Phosphodiesterase", *Molecular and Cellular Biol.* 1990, 10(6), 2678–2686.

Manhas et al., "heterocyclic Compounds XII. Quinazoline Derivatives as Potential Antifertility Agents(1)" *J. Heterocyclic Chem.*, 1979, 16, 711–715.

Meyers, A.J. et al., "Oxazolines. XI. Synthesis of Functionalized Aromatic and Aliphatic Acids. A Useful Protecting Group for Carboxylic Acids Against Grignard and Hydride Reagnets", *J. Org. Chem.* 1974, 39(18), 2787–2793.

Mezheritskaya, "Synthesis and properties of carboxonium het=erocyclic systems. VII. Synthesis and properties of 2–benzyl–substituted 1,3–dioxolanium salts", *Chem. Abstr.*, 1980, 93, 95160j, 635.

Mitsunobu, O., "The Use of Diethyl Azodicarboxylate and Triphenylphosphine in Synthesis and Transformation of Natural Products" *Synthesis*, 1981, 1–28.

Nicholson et al., "Differential Modulation of Tissue Function and Therapeutic Potential of Selective Inhibitors of Cyclic Nucleotide Phosphodiesterase Isoenzymes" *TIPS*, 1991, 12, 19–27.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.*, 1964, 60(8) #10203.4.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarbline", *J. Heterocyclic Chem.*, 1994, 31, 1311–1315.

Porter et al., "Preparation of 6–phenyl–3–(5–tetrazolyl)pyridine–=2(H)–one Derivatives as Cyclic AMP–dependent Protein Kinase Agonists" *Chem. Abstr.*, 1992, 117(9), 90296n.

Ramalingam, Deshmukh and Sattur, "Synthesis and Pharmacology of 2,5–Disubstituted 1,3,4–Zxadiazoles" *J. Indian Chem. Soc.*, 1981, 58(3), 269–271.

Reddy et al., "Inhibition of Breast Cancer Cell Growth in Vitro by a Tyrosine Kinase Inhibitor" *Cance Research*, 1992, 52, 3636–3641.

Sáchenz, H.I. et al., "Formal Total Syntehsis of β–Pipitzol", *Tetrahedron*, 1985, 41(12), 2355–2359.

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M. J. et al., "Synthetic Connections to the Aromatic Directed Metalation Reaction. Functionalized Aryl Boronic Acids by Ipso Borodesilylation; General Synthesis of Unsymmetrical iphenuyls and n–Terphenyls", *Tetrahedron Lett.*, 1987, 28(43), 5093–5096.

Thompson, W.J. and Gaudino, J., "A General Synthesis of 5–Arylnicotinates" *J. Org. Chem.*, 1984, 49, 5237–5243.

Yeadon et al., "Mechanisms Contributing to Ozone–Induced Bronchial Hyperreactivity in Guinea Pigs", *Pulmonary Pharm.*, 1992, 5, 39–50.

Yoneda et al., "The Antiproliferative Effects of Tyrosine Kinase Inhibitors Tyrophostins on a Human Squamous Cell Carcinoma in Vitro and in Nude Mice" *Cancer Research*, 1991, 51, 4430–4435.

Green & Wuts, "Protective Groups in Organic Synthesis", John Wiley & Sons, 1991.

Heaslip et al CA 120:208310.

Sakakibara, K. et al., "Preparation of N-pyridyl-4-(benzyloxy)benzamides as Cardiotonics", *Chem. Abstr.* 1988, 108, No. 131583p.

Tsutsumi, K. et al., "Preparation of (Dialkoxyphosphinoylmethyl)benzamides as Antihyperlipidemics", *Chem. Abstr.* 1990, 113, No. 6599a.

SUBSTITUTED OXIME DERIVATIVES AND PROCESSES FOR THEIR PREPARATION

This invention relatss to a novel series of substituted oxime derivatives, to processes for their preparation, to pharmaceutical compositions containing them, and to their use in medicine.

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I-VII) the distribution of Which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11:150–155 and Nicholson etal (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effectis in inflammatory diseases such as asthma, by achieving both anti-inflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

We have now found a novel series of tri-substituted phenyl derivatives, members of which are potent inhibitors of PDE IV at concentrations at which they have little or no inhibitory action on other PDE isoenzymes. These compounds inhibit the human recombinant PDE IV enzyme and also elevate cAMP in isolated leukocytes. The compounds of the invention are therefore of use in medicine, especially in the prophylaxis and treatment of asthma.

Thus according to one aspect of the invention, we provide a compound of formula (1)

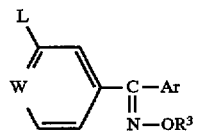

(1)

wherein
$=W-$ is (1)$=C(Y)-$ where Y is a halogen atom, or an alkyl or $-XR^a$ group where X is $-O-$, $-S(O)_m-$ [where m is zero or an integer of value 1 or 2], or $-N(R^b)-$ [where $R^b$ is a hydrogen atom or an optionally substituted alkyl group] and $R^a$ is a hydrogen atom or an optionally substituted alkyl group or, (2) $=N-$;

L is a $-XR$, [where R is an optionally substituted alkyl, alkenyl, cycloalkyl or cyloalkenyl group], $-C(R^5)=C(R^1)(R^2)$ or $[-CH(R^5)]_nCH(R^1)(R^2)$ group where $R^5$ is a hydrogen or a fluorine atom or a methyl group, and $R^1$ and $R^2$, which may be the same or different, is each a hydrogen or fluorine atom or an optionally substituted alkyl, alkenyl, alkynyl, alkoxy, alkylthio, $-CO_2R^6$, [where $R^6$ is a hydrogen atom or an optionally substituted alkyl, aralkyl, or aryl group], $-CONR^7R^8$ [where $R^7$ and $R^8$, which may be the same or different are as defined for $R^6$], $-CSNR^7R^8$, $-CN$ or $-NO_2$ group, or $R^1$ and $R^2$ together with the C atom to which they are attached are linked to form an optionally substituted cycloalkyl or cycloalkenyl group and n is zero or the integer 1;

Ar is a group $-(CH_2)_n-Z-Ar'$ where Ar' is an optionally substituted monocyclic or bicyclic heteroaryl group and Z is a bond, an atom $-O-$, or $-S-$ or a group $-N(R^b)-$ and n is zero or the integer 1, 2, 3 or 4; $R^3$ is a hydrogen atom, or an optionally substituted alkyl, alkenyl, alkynyl, $-C(O)R^4$ (where $R^4$ is an amino, alkylamino, arylamino, aryl, aryloxy, alkoxy or an optionally substituted alkyl group) or $-C(S)R^4$ group; and the salts, solyates, hydrates, prodrugs, and N-oxides thereof.

Compounds of formula (1) may exist as geometric isomers and the invention is to be understood to extend to all such isomers and mixtures thereof.

In the compounds of formula (1), when $=W-$ is $=C(Y)-$ and Y is a halogen atom Y may be for example a fluorine, chlorine, bromine or iodine atom.

When W in the compounds of formula (1) is a group $=C(Y)-$ and Y is $-XR^a$, $R^a$ may be, for example, a hydrogen atom or an optionally substituted straight or branched alkyl group, for example, an optionally substituted $C_{1-6}$alkyl group, such as a methyl, ethyl, n-propyl or i-propyl group. Optional substituents which may be present on $R^a$ groups include one or more halogen atoms, e.g. fluorine, or chlorine atoms. Particular $R^a$ groups include for example $-CH_2F$, $-CH_2Cl$, $-CHF_2$, $-CHCl_2$, $-CF_3$ or $-CCl_3$ groups.

When $=W-$ in the compounds of formula (1) is a group $=C(Y)-$ where $-Y$ is $-N(R^b)$, $=W-$ may be a $=C(NH_2)-$, $=C(NHC_3)-$ or $=C(NHC_2H_5)-$ group.

In compounds of formula (1), X may be an oxygen or a sulphur atom, or a group $-S(O)-$, $-S(O)_2-$, $-NH-$ or $C_{1-6}$alkylamino, for example a $C_{1-3}$alkylamino, e.g. methylamino [$-N(CH_3)-$] or ethylamino [$-N(C_2H_5)-$] group.

Alkyl groups represented by Y, R, $R^1$, $R^2$ or $R^b$ in the compounds of formula (1) include optionally substituted straight or branched $C_{1-6}$alkyl groups optionally interrupted by one or more X atoms or groups. Particular examples include $C_{1-3}$alkyl groups such as methyl or ethyl groups. Optional substituents on these groups include one, two or three substituents selected from halogen atoms, e.g. fluorine, chlorine, bromine or iodine atoms, or hydroxyl or $C_{1-6}$alkoxy e.g. $C_{1-3}$alkoxy such as methoxy or ethoxy or $-CO_2R^6$, $-CONR^7R^8$, $-CSNR^7R^8$ or $-CN$ groups.

Alkenyl groups represented by R, $R^1$ or $R^2$ in the compounds of formula (1) include optionally substituted straight or branched $C_{2-6}$alkenyl groups optionally interrupted by one or more X atoms or groups. Particular examples include ethenyl, propen-1-yl and 2-methylpropen-1-yl groups. Optional substituents include those described above in relation to alkyl groups represented by the groups $R^1$ or $R^2$.

Alkynyl groups represented by $R^1$ or $R^2$ in compounds of formula (1) include optionally substituted straight or branched $C_{2-6}$alkynyl groups optionally interrupted by one or more X atoms or groups. Particular examples include ethynyl and propyn-1-yl groups. Optional substituents include those described above in relation to alkyl groups represented by the groups $R^1$ or $R^2$.

When $R^1$ or $R^2$ in compounds of formula (1) is an alkoxy or alkylthio group it may be for example an optionally substituted straight or branched $C_{1-6}$alkoxy or $C_{1-6}$alkylthio group optionally interrupted by one or more X atoms or groups. Particular examples include $C_{1-3}$alkoxy, e.g. methoxy or ethoxy, or $C_{1-3}$alkylthio e.g. methylthio or ethylthio groups. Optional substituents include those described above in relation to alkyl groups represented by the groups $R^1$ or $R^2$.

When $R^1$ and $R^2$ together with the carbon atom to which they are attached in the compounds of formula (1) are linked to form a cycloalkyl or cycloalkenyl group, the group may be for example a $C_{3-8}$cycloalkyl group such as a cyclobutyl, cyclopentyl or cyclohexyl group or a $C_{3-8}$cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups.

When R in the compounds of formula (1) is an optionally substituted cycloalkyl or cycloalkenyl group it may be for example a $C_{3-8}$cycloalkyl group such as a cyclobutyl, cyclopentyl or cyclohexyl group or a $C_{3-8}$cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups.

Alkyl groups represented by $R^3$ or $R^4$ in compounds of formula (1) include optionally substituted straight or branched $C_{1-6}$alkyl groups, e.g. $C_{1-3}$alkyl groups such as methyl, ethyl, n-propyl or i-propyl groups. Optional substituents which may be present on these groups include one or more halogen atoms, e.g. fluorine, chlorine, bromine or iodine atoms, or hydroxyl, $C_{1-6}$alkoxy e.g. $C_{1-3}$alkoxy such as methoxy or ethoxy groups, Ar' where Ar' is as described above, or aryl e.g. optionally substituted $C_{6-12}$aryl, e.g. phenyl groups.

Alkenyl or alkynyl groups represented by $R^3$ in compounds of formula (1) include $C_{2-6}$alkenyl or $C_{2-6}$alkynyl groups as described previously for $R^1$ groups. Such groups may be substituted, for example by one or more of the substituents listed above for alkyl groups represented by $R^3$.

Alkylamino groups represented by the group $R^4$ in compounds of formula (1) include optionally substituted straight or branched $C_{1-6}$alkylamino groups such as methylamino, ethylamino or propylamino groups. Optional substituents which may be present include those described above in connection with alkyl groups represented by the group $R^4$.

When $R^4$ is an arylamino group it may be for example a —NHAr" group where Ar" is an optionally substituted $C_{6-12}$aryl group, e.g. an optionally substituted phenyl group. Optional substituents include $R^9$ substituents described below.

Alkoxy groups represented by $R^4$ include optionally substituted straight or branched $C_{1-6}$alkoxy, e.g. methoxy, ethoxy or propoxy groups. Optional substituents which may be present include those described above in connection with alkyl groups represented by the group $R^4$.

Aryl groups represented by $R^4$ include —Ar" groups [where Ar" is as just defined], for example optionally substituted phenyl groups.

When $R^3$ in compounds of formula (1) is a —$COR^4$ or $CSR^4$ group, it may be for example a —$CONH_2$, —$CONR^7R^8$, [where $R^7$ and $R^8$ are as described below], —$CONHR^8$, —$CSNH_2$, —$CSNR^7R^8$, —$CSNHR^8$, —$COR^7$, —$CSR^7$, —$C(O)OR^7$, or —$C(S)OR7$ group.

When $R^1$ or $R^2$ is a —$CO_2R^6$, —$CONR^7R^8$ or $CSNR^7R^8$ group it may be for example a —$CO_2H$, —$CONH_2$ or —$CSNH_2$ group or a group —$CO_2R^6$, —$CONR^7R^8$, —$CSNR^7R^8$, —$CONHR^8$ or —$CSNHR^8$ where $R^6$, $R^7$ and $R^8$ where present is a $C_{1-3}$alkyl group such as methyl or ethyl group, a $C_{6-12}$aryl group, for example an optionally substituted phenyl, or a 1- or 2-naphthyl group, or a $C_{6-12}$aryl $C_{1-3}$alkyl group such as an optionally substituted benzyl or phenethyl group. Optional substituents which may be present on these aryl groups include $R^9$ substituents discussed below in relation to the group Ar.

Monocyclic or bicyclic heteroaryl groups represented by Ar' include for example a $C_{1-9}$ optionally substituted heteroaryl group containing for example one, two, three or four heteroatoms selected from oxygen, sulphur or nitrogen atoms. Monocyclic heteroaryl groups include for example five- or six-membered heteroaryl groups containing one, two, three or four heteroatoms selected from oxygen, sulphur or nitrogen atoms. Bicyclic heteroaryl groups include for example nine- or ten-membered heteroaryl groups containing one, two or more heteroatoms selected from oxygen, sulphur or nitrogen atoms.

Examples of heteroaryl groups represented by Ar' include pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl. Example of bicyclic heteroaryl groups include quinolinyl or isoquinolinyl groups.

The heteroaryl group represented by Ar' may be attached to the remainder of the molecule of formula (1) through any ring carbon or heteroatom as appropriate. Thus, for example, when the group Ar' is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group. In another example, when the group Ar' is a quinolinyl group it may be a 2-, 3-, 4-, 5-, 6-, 7- or 8-quinolinyl and when it is an isoquinolinyl, it may be a 1-, 3-, 4-, 5-, 6-, 7- or 8-isoquinolinyl group.

When in compounds of formula (1) the Ar' group is a nitrogen-containing heterocycle it may be possible to form quaternary salts, for example N-alkyl quaternary salts and the invention is to be understood to extend to such salts. Thus for example when the group Ar' is a pyridyl group, pyridinium salts may be formed, for example N-alkylpyridinium salts such as N-methylpyridinium.

The heteroaryl groups represented by Ar' in compounds of formula (1) or aryl substituents present on $R^3$ groups may each optionally be substituted by one, two, three or more substituents [$R^9$]. The substituent $R^9$ may be selected from an atom or group $R^{10}$ or —Alk$^2$($R^{10}$)$_m$ wherein $R^{10}$ is a halogen atom, or an amino (—NH$_2$), substituted amino, nitro, cyano, hydroxyl (—OH), substituted hydroxyl, cycloalkyl, cycloalkoxy, formyl [HC(O)—], carboxyl (—CO$_2$H), esterified carboxyl, thiol (—SH), substituted thiol, —Ar', —Ar (where Ar is an aryl group), —XAr', —XAr, —C(O)Alk$^2$, —SO$_3$H, —SO$_2$Alk$^2$, —SO$_2$NH$_2$, —SO$_2$NHAlk$^2$, —SO$_2$N[Alk$^2$]$_2$, —SO$_2$NHAr, —SO$_2$N(Alk$^2$)Ar, CONH$_2$, —CONHAlk$_2$, —CON[Alk$^2$]$_2$, —CONHAr, —CON(Alk$^2$)Ar, —NHSO$_2$H, —NAlk$^2$SO$_2$H, —NHSO$_2$Alk$^2$, —N[SO$_2$Alk$^2$]$_2$, —NHSO$_2$NH$_2$, —NAlk$^2$SO$_2$NH$_2$, —NHSO$_2$NHAlk$^2$, —NAlk$^2$SO$_2$NHAlk$^2$, —NHSO$_2$N[Alk$^2$]$_2$, —NAlk$^2$SO$_2$N[Alk$^2$]$_2$, —NAlk$^2$SO$_2$NHAlk$^2$, —NHSO$_2$NHAr, —NAlk$^2$SO$_2$NHAr, —NAlk$^2$SO$_2$NAlk$^2$Ar, —NHSO$_2$NAlk$^2$Ar, —NHC(O)H, —NHC(O)Alk$^2$, —NAlk$^2$C(O)H, —NAlk$^2$C(O)Alk$^2$, —N[C(O)Alk$^2$]$_2$, —NHC(O)OH, —NHC(O)OAlk$^2$, —NAlk$^2$C(O)OH, —NAlk$^2$C(O)OAlk$^2$, —N[C(O)H]SO$_2$H, —N[C(O)Alk$^2$]SO$_2$H, —N[C(O)H]SO$_2$Alk$^2$, N[C(O)Alk$^2$]SO$_2$Alk$^2$, —C(S)H, C(S)Alk$^2$, —CSNH$_2$, —CSNHAlk$^2$, —CSN[Alk$^2$]$_2$, —CSNHAr, —CSN(Alk$^2$)Ar, —NHC(S)Alk$^2$, —NAlk$^2$C(S)Alk$^2$, —N[C(S)Alk$^2$]SO$_2$H, —N[C(S)Alk$^2$]SO$_2$Alk$^2$, —NHCONH$_2$, —NHCONH(Alk$^2$), —NHCON[Alk$^2$]$_2$, —NAlk$^2$CONH$_2$, —NAlk$^2$CONH(Alk$^2$), —NAlk$^2$CON[Alk$^2$]$_2$, —NHCSNH$_2$, —NHCSNH(Alk$^2$), —NHCSN[Alk$^2$]$_2$, —NAlk$^2$CSNH$_2$, —NAlk$^2$CSNH(Alk$^2$), or —NAlk$^2$CSN[Alk$^2$]$_2$ group, Alk$^2$ is an optionally substituted straight or branched C$_{1-6}$alkylene, C$_{2-6}$alkenylene, or C$_{2-6}$alkynylene chain optionally interrupted by one, two, or three —O—, or —S— atoms or —S(O)$_p$—, [where p is an integer 1 or 2] or —N(R$^b$)— groups; and m is zero or an integer 1, 2 or 3.

When in the group —Alk$^2$(R$^{10}$)$_m$ is an integer 1, 2 or 3, it is to be understood that the substituent or substituents $R^{10}$ may be present on any suitable carbon atom in —Alk$^2$. Where more than one $R^{10}$ substituent is present these may be the same or different and may be present on the same or different carbon atom in Alk$^2$. Clearly, when m is zero and no substituent $R^{10}$ is present or when Alk$^2$ forms part of a group such as —SO$_2$Alk$^2$ the alkylene, alkenylene or alkynylene chain represented by Alk$^2$ becomes an alkyl, alkenyl or alkynyl group.

When $R^{10}$ is a substituted amino group it may be a group —NH[Alk$^2$(R$^{10a}$)$_m$] [where Alk$^2$ and m are as defined above and $R^{10a}$ is as defined above for $R^{10}$ but is not a substituted amino, a substituted hydroxyl or a substituted thiol group] or a group —N[Alk$^2$(R$^{10a}$)$_m$]$_2$ wherein each —Alk$^2$(R$^{10a}$)$_m$ group is the same or different.

When $R^{10}$ is a halogen atom it may be for example a fluorine, chlorine, bromine, or iodine atom.

When $R^{10}$ is a cycloalkoxy group it may be for example a C$_{5-7}$cycloalkoxy group such as a cyclopentyloxy or cyclohexyloxy group.

When $R^{10}$ is a substituted hydroxyl or substituted thiol group it may be a group —OAlk$^2$(R$^{10a}$)$_m$ or —SAlk$^2$(R$^{10a}$)$_m$ respectively, where Alk$^2$, $R^{10a}$ and m are as just defined.

Esterified carboxyl groups represented by the group $R^{10}$ include groups of formula —CO$_2$Alk$^3$ wherein Alk$^3$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$alkyl group such as an optionally substituted phenyloxymethyl, phenyloxyethyl, 1-naphthyloxymethyl, or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the Alk$^3$ group include $R^9$ substituents described above.

Particular examples of the chain Alk$^2$ when present in compounds of formula (1) include methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^b$)— groups.

Particularly useful atoms or groups represented by $R^9$ include fluorine, chlorine, bromine or iodine atoms, or C$_{1-6}$alkyl, e.g. methyl or ethyl, C$_{1-6}$alkylamino, e.g. methylamino or ethylamino, C$_{1-6}$hydroxyalkyl, e.g. hydroxymethyl or hydroxyethyl, C$_{1-6}$alkylthiol e.g. methylthiol or ethylthiol, C$_{1-6}$alkoxy, e.g. methoxy or ethoxy, C$_{5-7}$cycloalkyl, e.g. cyclopentyl, C$_{5-7}$cycloalkoxy, e.g. cyclopentyloxy, haloC$_{1-6}$alkyl, e.g. trifluoromethyl, C$_{1-6}$alkylamino, e.g. methylamino or ethylamino, amino (—NH$_2$), aminoC$_{1-6}$alkyl, e.g. aminomethyl or aminoethyl, C$_{1-6}$dialkylamino, e.g. dimethylamino or diethylamino, nitro, cyano, hydroxyl (—OH), formyl [HC(O)—], carboxyl (—CO$_2$H), —CO$_2$Alk$^3$ [where Alk$^3$ is as defined above], C$_{1-6}$alkanoyl e.g. acetyl, C$_{1-6}$thiocarbonyl e.g. thioacetyl, thiol (—SH), thio C$_{1-6}$alkyl, e.g. thiomethyl or thioethyl, C$_{6-12}$aryl, e.g. phenyl, C$_{6-12}$aryloxy, e.g. phenoxy, C$_{6-12}$aralkyl, e.g. benzyl, C$_{6-12}$aralkoxy e.g. benzyloxy, sulphonyl (—SO$_3$H), C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylamino-sulphonyl, C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, phenylaminocarbonyl, sulphonylamino (—NHSO$_2$H), C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, phenylaminosulphonylamino, C$_{1-6}$alkanoylamino, e.g. acetylamino, C$_{1-6}$alkanoylaminoC$_{1-6}$alkyl e.g. acetylaminomethyl or C$_{1-6}$alkoxycarbonylamino, e.g. methoxycarbonylamino, ethoxycarbonylamino or t-butoxycarbonylamino, thiocarboxamido (—CSNH$_2$), C$_{1-6}$alkylaminothiocarbonyl, e.g. methylaminothiocarbonyl or ethylaminothiocarbonyl, C$_{1-6}$dialkylaminothiocarbonyl, e.g. dimethylaminothiocarbonyl or diethylaminothiocarbonyl, phenylaminothiocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, aminothiocarbonyiamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino, or diethylaminothiocarbonylamino, aminocarbonyl$C_{1-6}$alkylamino, e.g. aminocarbonylmethylamino or aminocarbonylethylamino, aminothiocarbonyl$C_{1-6}$alkylamino e.g. aminothiocarbonylmethylamino or aminothiocarbonylethylamino, formylamino$C_{1-6}$alkylsulphonylamino, e.g. formylaminomethylsulphonylamino or formylaminoethylsulphonylamino, thioformylamino$C_{1-6}$alkylsulphonylamino, e.g. thioformylaminomethylsulphonylamino or thioformylethylsulphonylamino, $C_{1-6}$acylaminosuiphonylamino, e.g. acetylaminosulphonylamino, $C_{1-6}$thioacylaminosulphonylamino, e.g. thioacetylaminosulphonylamino groups.

Where desired, two $R^9$ substituents may be linked together to form a cyclic group such as a cyclic ether, e.g. a $C_{2-6}$alkylenedioxy group such as ethylenedioxy.

It will be appreciated that where two or more $R^9$ substituents are present, these need not necessarily be the same atoms and/or groups. The $R^9$ substituents may be present at any ring carbon atom away from that attached to the rest of the molecule of formula (1).

When in the compounds of formula (1) the group Ar is a —(CH$_2$)$_n$—Z—Ar' group, the group may be for example an —Ar, —CH$_2$Ar', —(CH$_2$)$_2$ Ar', —(CH$_2$)$_3$—Ar',—(CH$_2$) OAr', —(CH$_2$)$_2$OAr', (—CH$_2$)$_3$OAr', —CH$_2$—S—Ar', —(CH$_2$)$_2$—S—Ar', —(CH$_2$)$_3$—S—Ar', —CH$_2$—N(R$^b$)—Ar', —(CH$_2$)$_2$—N(R$^b$)—Ar' or —(CH$_2$)$_3$—N(R$^b$)—Ar' group.

In the compounds of formula (1), when an ester group is present, for example a group CO$_2$R$^6$ or —CO$_2$Alk$^3$ this may advantageously be a metabolically labile ester.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, pipeddine, dimethylamine or diethylamine salts.

Prodrugs of compounds of formula (1) include those compounds, for example esters, alcohols or amines, which are convertible in vivo by metabolic means, e.g. by hydrolysis, reduction, oxidation or transesterification, to compounds of formula (1).

Particularly useful salts of compounds according to the invention include pharmaceutically acceptable salts, especially acid addition pharmaceutically acceptable salts.

In the compounds of formula (1) the group =W— is preferably a =C(Y)— group. In compounds of this type Y is preferably a —XR$^a$ group where X is —O— and R$^a$ is an optionally substituted ethyl group or, especially, an optionally substituted methyl group. Especially useful substituents which may be present on R$^a$ groups include one, two or three fluorine or chlorine atoms.

One particularly useful group of compounds of the invention has the formula (1) where L is a group —XR. In compounds of this type X is preferably —O—. The group R in these compounds is preferably an optionally substituted cycloalkyl group, particularly an optionally substituted cyclopentyl group, and is, especially a cyclopentyl group.

In another group of compounds of formula (1) L is preferably a —CH=C(R$^1$)(R$^2$) group. In compounds of this type R$^1$ and R$^2$ are preferably linked together with the C atom to which they are attached to form an optionally substituted cycloalkyl or cycloalkenyl group, especially a substituted cyclopentyl or cyclohexyl or, especially, a cyclopentyl or cyclohexyl group.

When in compounds of formula (1) Ar' is a substituted pyridyl group it may be for example a mono-or disubstituted pyridyl group, such as a mono- or disubstituted 2-pyridyl, 3-pyridyl or especially 4-pyridyl group substituted by one or two atoms or groups $R^9$ as defined above, in particular one or two halogen atoms such as fluorine or chlorine atoms, or methyl, methoxy, hydroxyl or nitro groups. Particularly useful pyridyl groups of these types are 3-monosubstituted-4-pyridyl or 3,5-disubstituted-4-pyridyl, or 2- or 4-monosubstituted-3-pyridyl or 2,4-disubstituted-3-pyridyl groups.

A particularly useful group of compounds of formula (1) has the formula (2):

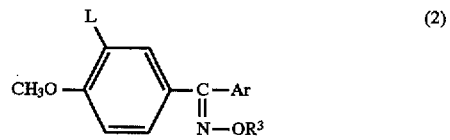

where —L is OR, where R is an optionally substituted cycloalkyl group, —CH=C(R$^1$)(R$^2$) or —CH$_2$CH(R$^1$)(R$^2$) group where R$^1$ and R$^2$ are linked together with the carbon atom to which they are attached to form a cycloalkyl group; Ar and R$^3$ are as defined for formula (1); and the salts, solvates, hydrates, prodrugs and N-oxides thereof.

In general in compounds of formulae (1) and (2) Ar is preferably a —Ar' or —CH$_2$Ar' group. In compounds of this type, and in general, Ar' is preferably an optionally substituted pyridyl group, particularly as specifically described previously.

In one particular group of compounds of formulae (1) and (2) the group $R^3$ is preferably a hydrogen atom, or a —CONH$_2$, or —COR$^7$ group, where R$^7$ is an optionally substituted alkyl, especially methyl or ethyl, or phenyl group.

Particularly useful compounds of formula (1) according to the invention are the (E) and/or (Z) isomers of:

1-(3-cyclopentyloxy-4-methoxyphenyl)-2-(2,6-dichloro-4-pyridyl)ethanone oxime;

0-(aminocarbonyl)-1-(3-cyclopentyloxy-4-methoxy-phenyl)-2-(2,6-dichloropyrid-4-yl)ethanone oxime;

0-propanoyl-1 -(3-cyclopentyloxy-4-methoxy-phenyl)-2-(2,6-dichloropyrid-4-yl)ethanone oxime;

0-benzoyl-2-(2,6-dichloropyridyl)-1-(3-cyclopentyl-oxy-4-methoxyphenyl)ethanone oxime;

0-methyl-1-(3-cyclopentyloxy-4-methoxyphenyl)-2-[4-(2,6-dichloropyridine)]ethanone oxime; and the salts, solvates, hydrates, prodrugs and N-oxides thereof.

Compounds according to the invention are selective and potent inhibitors of PDE IV. The ability of the compounds to act in this way may be simply determined by the tests described in the Examples hereinafter.

The compounds according to the invention are thus of particular use in the prophylaxis and treatment of human diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention may also reduce gastric acid secretion and therefore can be used to treat conditions associated with hypersecretion.

Compounds of the invention may suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention may suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections or in diseases such as cancer, leads to cachexia and muscle wasting. Compounds of the invention may ameliorate these symptoms with a consequent enhancement of quality of life.

Compounds of the invention may also elevate cAMP in certain areas of the brain and thereby counteract depression and memory impairment.

Compounds of the invention may suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants. (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formulae (1) and (2) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogan-free water, before use.

In addition to the formulations described above, the compounds of formulae (1) and (2) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable properlant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg, e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds according to the invention may be prepared by the following processes. The symbols W, L, $L^1$, Z, X, $R^1$, $R^2$, $R^3$, $R^4$ and $R^5$ when used in the formulae below are to be understood to represent those groups described above in relation to formula (1) unless otherwise indicated. In the reactions described below it may be necessary to protect reactive functional groups, for example hydroxy, amino, thio, carboxy or aldehyde groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981].

Thus according to a further aspect of the invention, compounds of formula (1) may be prepared by reacting a compound of formula (3)

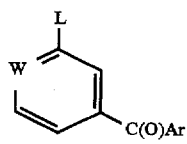
(3)

with a hydroxylamine NH$_2$OR$^3$ or a salt thereof.

The reaction may be performed at an elevated temperature, e.g. the reflux temperature and where necessary in the presence of a base, for example, an organic base such as pyridine.

This reaction is particularly suitable for the preparation of compounds of formula (1) where R$^3$ is a hydrogen atom.

Intermediates of formula (3) may be prepared by oxidation of an alcohol of formula (4)

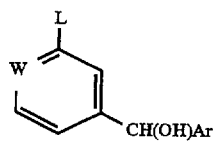
(4)

using an oxidising agent, such as oxalyl chloride (COCl)$_2$ in the presence of dimethylsulphoxide and thriethylamine in a solvent, e.g. dichloromethane.

Intermediates of formula (4) may be prepared by reaction of an aldehyde of formula (5)

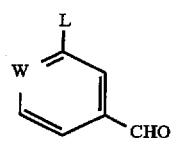
(5)

with an organometallic reagent Ar—M [where M is a metal atom, for example a lithium atom] in a solvent such as an ether, e.g. a cyclic ether such as tetrahydrofuran, at a low temperature e.g. around −70° C. to ambient temperature.

Reagents Ar—M are either known compounds or may be prepared, preferably in situ during the above process, by reaction of a compound AlkCH$_2$M or [Alk]$_2$NM [where Alk is an alkyl group such as a n-propyl or i-propyl group] with a compound ArH using the just mentioned reaction conditions.

Intermediates of formula (5) where L is a —XR group in which X is —O—, —S— or —N(R$^b$)— may be prepared by alkylation of an intermediate of formula (6)

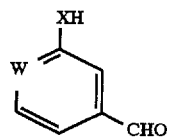
(6)

using the reagents and conditions described below for the preparation of a compound of formula (1) from an intermediate of formula (10).

Intermediates of formula (6) are known compounds or may be prepared from known starting materials using similar conditions to those used to prepare the known compounds.

Intermediates of formula (5) where —W═ is —N═ may be prepared from an intermediate of formula (7)

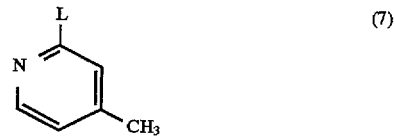
(7)

by successive oxidation and reduction reactions.

For example, a first oxidation by SeO$_2$ or potassium permanganate gives the carboxylic acid derivative. This in turn is reduced by a reducing agent, for example lithium aluminium hydride to give the alcohol, which, upon oxidation with manganese dioxide gives the desired intermediate (5).

Intermediates of formula (7) may be prepared by reacting a halide of formula (8)

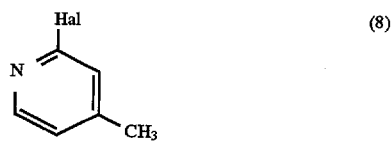
(8)

where Hal is a halogen atom, e.g. a bromine, chlorine or iodine atom with a compound RXH, where X is —O—, —S— or —NH— in the presence of a base.

Bases used in this reaction include hydrides, such as sodium hydride, or an organometallic base, such as butyl-lithium in a solvent, such as an amide, for example dimethylformamide at a temperature from room temperature to above, e.g. 80° C.

Intermediates of formula (8) may be prepared by reacting an amine of formula (9)

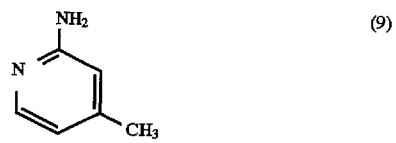
(9)

with nitrous acid (made in situ by reacting sodium nitrite with an acid, for example sulphuric acid or hydrobromic acid) to produce the diazonium salt. This in turn may be reacted with a haloacid, e.g. hydrobromic, hydrochloride or hydriodic acid if necessary in the presence of the corresponding copper (1) halide for example CuBr or CuI or halogen, e.g. Br$_2$, Cl$_2$ or I$_2$.

In another process according to the invention, a compound of formula (1) where L is a —XR group in which X is —O—, —S— or —N(R$^b$)— may be prepared by alkylation of a compound of formula (10):

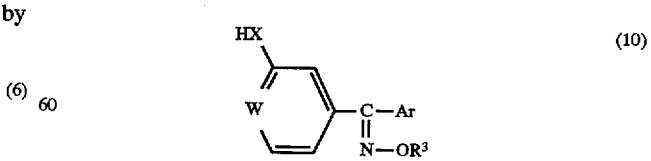
(10)

using a reagent RL$^1$, where L$^1$ is a leaving group.

Leaving groups represented by L$^1$ include halogen atoms such as iodine, chlorine or bromine atoms or sulphonyloxy groups such as arylsulphonyloxy groups, e.g. p-toluenesulphonyloxy.

The alkylation reaction may be carried out in the presence of a base, e.g. an inorganic base such as a carbonate, e.g. cesium or potassium carbonate, an alkoxide, e.g. potassium-t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at ambient temperature or above e.g. around 40° C. to 50° C.

Intermediates of formula (10) may be obtained from the corresponding protected compound of formula (11):

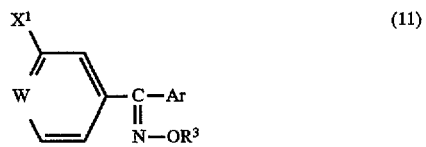

wherein $X^1$ is a protected hydroxy, thio or amino group using conventional procedures [see Green, T. W. ibid]. Thus, for example, where X is a t-butyldimethylsilyloxy group, the required hydroxyl group may be obtained by treatment of the protected intermediate with tetrabutylammonium fluoride. The protected intermediate of formula (11) may be prepared in an analogous manner to the compounds of formula (1) using the reactions described herein and appropriately protected intermediates.

In a further process according to the invention, compounds of general formula (1) where L is a —C($R^5$)=C($R^1$)($R^2$) group and $R^5$ is a hydrogen atom or a methyl group, may be prepared by coupling a compound of formula (12)

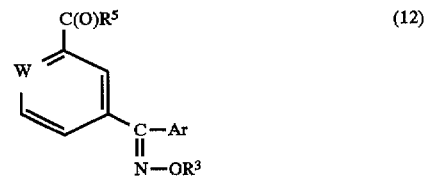

where $R^5$ is as described above with an olefination agent.

Particular examples of olefination agents include phosphonium salts such as compounds $(R^1)(R^2)$CHP$(D)_3$Hal where Hal is a halogen atom, such as a bromine atom, and D is an optionally substituted alkyl, e.g. methyl, or aryl, especially phenyl, group; phosphoranes $(R^1)(R^2)$C=P$(D)_3$; phosphonates $(DO)_2$P(O)CH$(R^1)(R^2)$; or silane derivatives, for example compounds of formula $(D)_3$SiC$(R^1)(R^2)$, e.g. trialkylsilanes such as $(CH_3)_3$SiC$(R^1)(R^2)$.

Bases for use in the above reaction include organometallic bases, for example, an organolithium compound such as an alkyllithium e.g. n-butyllithium, a hydride, such as sodium or potassium hydride or an alkoxide, such as a sodium alkoxide, e.g. sodium methoxide.

The reaction may be performed in a suitable solvent, for example a polar aprotic solvent, such as an alkyl sulphoxide, e.g. methyl sulphoxide, an amide such as N,N-dimethylformamide or hexamethyl-phosphorous triamide; a non-polar solvent, such as an ether, e.g. tetrahydrofuran or diethyl ether or an aromatic solvent such as benzene, toluene or xylene; or a polar protic solvent, such as an alcohol, for example ethanol. Preferably the reaction is carried out at a low temperature, for example from around −78° C. to around room temperature.

The olefination agents used in this reaction are either known compounds or may be prepared from known starting materials using reagents and conditions similar to those used to prepare the known compounds. For example, a phosphorane may be prepared in situ by reaction of a phosphonium salt with a base of the type described above. In another example, a phosphonate may be prepared by reacting a halide $(R^1)(R^2)$CHHal with a phosphite $(DO)_3$P, as described in the Arbuzov reaction. Silane derivatives may be prepared by reaction of a halosilane $(D)_3$SiHal with a base, such as lithium diisopropylamide, in a solvent, such as an ether, for example a cyclic ether, e.g. tetrahydrofuran, at low temperature, e.g. −10° C.

Intermediates of formula (12) where $R^5$ is a methyl group, may be prepared by reacting an intermediate of formula (12) where $R^5$ is a hydrogen atom with an organometallic reagent, such as methyllithium or $CH_3$MgHal, using the conditions just described followed by oxidation of the resulting alcohol, using an oxidising agent, e.g. manganese dioxide.

Intermediates of formula (12) where $R^5$ is a hydrogen atom may be prepared by deprotecting a protected aldehyde of formula (13)

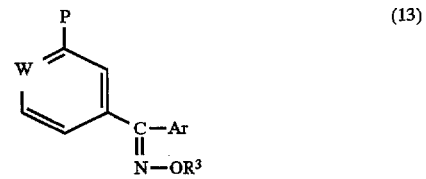

where P is a protected aldehyde group, e.g. a dioxanyl group, using acid hydrolysis e.g. by reaction with trifluoroacetic acid or p-toluene sulphonic acid, in the presence of a solvent, e.g. acetone, or a mixture of solvents, e.g. chloroform and water.

Intermediates of formula (13) may be prepared in several steps from the protected intermediates of formula (14)

using similar reagents and conditions described herein above for the preparation of compounds of formula (1) from intermediates of formula (5).

According to a further aspect of the invention compounds of formula (1) where L is a group —C($R^5$)=CH($R^1$) and $R^1$ is an optionally substituted alkyl, alkenyl or alkynyl group may also be prepared by reaction of an intermediate of formula (12) with an organometallic reagent, followed by dehydration of the resulting alcohol.

Examples of organometallic reagents include organolithium $R^1$Li or organomagnesium $R^1$MgHal reagents. The reaction with the organometallic reagent may be performed in a solvent such as an ether, such as diethyl ether or for example a cyclic ether such as tetrahydrofuran, at a low temperature for example −10° C. to room temperature. The dehydration may be performed using an acid, for example an organic acid such as p-toluene sulphonic acid or trifluoroacetic acid, in the presence of a base, such as an amine, e.g. triethylamine.

In another aspect of the invention, compounds of general formula (1) where L is a —C($R^5$)=C($R^1$)($R^2$) or [CH($R^5$)$_n$] CHR$^1$R$^2$ group may be prepared by reacting a compound of formula (10) wherein X is —O— with (1) a triflate reagent, such as trifluoromethanesulphonic anhydride, to give the aryltriflate derivative; followed by reaction with (2) an organostannane.

The reaction (1) may take place in a solvent, for example a halogenated solvent, such as dichloromethane, or an amine, such as pyridine, or a mixture of solvents, e.g. dichloromethane and pyridine, at a low temperature e.g. around 0° C.

The aryltriflate is then coupled with an organostannane, in the presence of a palladium catalyst and lithium chloride. Examples of organostannane include alkenylstannate, e.g. tri-n-butylethenylstannane, alkylstannate, e.g. tetra-n-butylstannate, or alkynylstannate, e.g. tri-n-butynylstannate. The palladium catalysts include bis(triphenyl-phosphine) palladium (II) [Pd(Cl$_2$PPh$_3$)$_2$] or tetrakis (triphenylphosphine)palladium (O) [Pd(PPh$_3$)$_4$]. The reaction may take place in a solvent, such as an ether e.g. dioxane or THF or an amide, e.g. DMF, at an elevated temperature, e.g. at reflux.

Compounds of formula (1) may be prepared by interconversion of another compound of formula (1). For example, a compound of formula (1) where L is a —CH(R$^5$)CHR$^1$R$^2$ group may be prepared by hydrogenation of a compound of formula (1) where L is a C(R$^5$)=C(R$^1$)(R$^2$) group. The hydrogenation may be performed using for example hydrogen in the presence of a catalyst. Suitable catalysts include metals such as platinum or palladium optionally supported on an inert carrier such as carbon or calcium carbonate; nickel, e.g. Raney nickel, or rhodium. The reaction may be performed in a suitable solvent, for example an alcohol such as methanol or ethanol, an ether such as tetrahydrofuran or dioxane, or an ester such as ethyl acetate, optionally in the presnce of a base, for example a tertiary organic base such as triethylamine, at for example ambient temperature.

The organostannates are known compounds or may be prepared from known reagents using conditions similar to those used to prepare the known compounds.

Alternatively, the reaction may be accomplished by transfer hydrogenation using an organic hydrogen donor and a transfer agent. Suitable hydrogen donors include for example acids, such as formic acid, formates, e.g. ammonium formate, alcohols, such as benzyl alcohol or ethylene glycol, hydrazine, and cycloalkenes such as cyclohexene or cyclohexadiene. The transfer agent may be for example a transition metal, for example palladium or platinum, optionally supported on an inert carrier as discussed above, nickel e.g. Raney nickel, ruthenium, e.g. tris (triphenylphosphine) ruthenium chloride or copper. The reaction may generally be performed at an ambient or elevated temperature, optionally in the presence of a solvent, for example an alcohol such as ethanol or an acid such as acetic acid.

In another interconversion reaction, compounds of formula (1) where R$^3$ is an alkyl, alkenyl or alkynyl group, e.g. a methyl group, may be prepared by reaction of a compound of formula (1) where R$^3$ is a hydrogen atom with a diazo compound, such as diazomethane or an alkyl halide e.g. iodomethane or sulphate, if necessary in the presence of a base, such as a hydride, e.g. sodium hydride, and a catalyst, e.g. such as a quaternary ammonium salt, e.g. tetra-n-butylammonium iodide.

Compounds of formula (1) where R$^3$ is a —C(O)NH$_2$ group may be prepared by reacting a compound of formula (1), where R$^3$ is a hydrogen atom, with an isocyanate, such as chlorosulphonyl isocyanate ClSO$_2$NCO, or trichloroacetyl isocyanate Cl$_3$C(O)NCO (followed by reaction with ammonia) or sodium cyanate NaOCN, in a solvent such as a cyclic ether, e.g. tetrahydrofuran or a halogenated solvent, e.g. dichloromethane, if necessary in the presence of an acid, such as trifluoroacetic acid or acetic acid, at around room temperature.

Compounds of formula (1) where R$^3$ is a —C(O)R$^4$ group in which R$^4$ is an alkylamino or arylamino group may be prepared by reacting a compound of formula (1) where R$^3$ is a hydrogen atom with an isocyanate R$^4$—N=C=O (where R$^4$ is an alkyl or aryl group) in a solvent, e.g. tetrahydrofuran.

Compounds of formula (1) where R$^3$ is a —C(O)R$^4$ group in which R$^4$ is lower alkoxy or aryloxy group, may be prepared by reaction of a compound of formula (1) in which R$^3$ is a hydrogen atom with a reagent R$^4$OC(O)X (where R$^4$ is as just described and X is a leaving group, such as a halogen atom, for example a chlorine atom) in a solvent, e.g. dichloromethane.

Compounds of formula (1) where R$^3$ is a —C(O)R$^4$ group in which R$^4$ is an alkyl group, may be prepared by reacting a compound of formula (1) where R$^3$ is a hydrogen atom with (1) an alkylanhydride, such as propionic anhydride in a solvent or mixture of solvents such as dichloromethane and pyridine; or (2) with an acid chloride, where necessary in the presence of a base, such as an organic amine, e.g. pyridine.

In another example of an interconversion, a group represented by Ar' or R$^4$ in compounds of formula (1) may be substituted in the aryl or heteroaryl portions by any of the groups R$^9$ by an appropriate substitution reaction using the corresponding unsubstituted compound of formula (1) and a R$^9$containing nucleophile or electrophile.

In yet another example of an interconversion process a compound of formula (1) wherein R$^3$ is a —C(S)R$^4$ group and/or R$^4$ contains a —C(S)—, —C(S)N, or —NC(S)— group may be prepared by reacting a compound of formula (1) wherein R$^3$ is a —C(O)R$^4$ group and/or R$^4$ contains a —C(O)—, —C(O)N, or —NC(O)— group with a thiation reagent, such as Lawesson's reagent, in an anhydrous solvent, for example toluene, at an elevated temperature, such as the reflux temperature.

In a still further example of interconversion process, a compound of formula (1) wherein R$^3$ is not a hydrogen atom may be prepared by reacting a compound of formula (1) wherein R3 is a hydrogen with a diazocompound or an isocyanate R$^4$NCO, a reagent R$^4$OC(O)X as described hereinabove for the preparation of a compound of formula (1) from an intermediate of formula (3).

The following examples illustrate the invention. The following abbreviations are used: THF—tetrahydrofuran; Et2O—diethyl ether; EtOAc—ethyl acetate; LDA—lithium diisopropylamide; RT—room temperature; MeOH—methanol; DMSO—dimethyl sulphoxide; CH$_2$Cl$_2$ dichloromethane; HPLC—high performance liquid chromatography; DMF—dimethylformamide.

INTERMEDIATE 1

3-Cyclopentyloxy-4-methoxybenzaldehyde

The title comDound was prepared as described for Intermediate 1 in International Patent Specification No. WO 94/14742.

INTERMEDIATE 2

3,5-Dichloro-4-methylpyridine

The title compound was prepared as described for Intermediate 15 in International Patent Specification No. WO 94/14742.

INTERMEDIATE 3

(±)-4-2-(3-Cyclopentyloxy-4-methoxyphenyl)-2-hydroxyethyl-3,5-dichloropyridine

The title compound was prepared from Intermediate 2 as described in the compound of Example 1a) in International Patent Specification No. WO 94/20446.

INTERMEDIATE 4

(3-Cyclopentyloxy-4-methoxyphenyl)(3,5-dichloro-4-pyridylmethyl)ketone

A solution of DMSO (2.77 g, 35.5 mmol) in $CH_2Cl_2$ (15 ml) was added to a solution of oxalyl chloride (2.08 g, 16.4 mmol) in $CH_2Cl_2$ (40 ml) at ca. −70° C. After stirring at −20° C. for 0.25 h, a solution of Intermediate 3 (5.65 g, 14.8 mmol) in $CH_2Cl_2$ (90 ml) was added over 0.25 h and the reaction mixture maintained at <−50° C. for 0.5 h. Triethylamine (6.95 g, 68.7 mmol) was then added and the mixture allowed to warm to RT. The reaction mixture was quenched with water (75 ml) and extracted with $CH_2Cl_2$ (2×75 ml). The extract was washed with saturated sodium bicarbonate solution (30 ml), then brine (30 ml), dried ($MgSO_4$), and concentrated. in vacuo. The residue was subjected to chromatography ($SiO_2$; 1% MeOH—$CH_2Cl_2$) to afford the title compound (4.94 g) as an off-white solid m.p. 129°–130° C.; δH ($CDCl_3$) 1.5–2.1 (8H, br m, $CH_2)_4$), 3.95 (3H, s, OMe), 4.64 (2H, s, $COCH_2$), 4.85 (1 H, br m, OCH), 6.94 (1 H, d, J 8.4 Hz, ArH ortho to OMe), 7.57 (1H, d, J 2.0 Hz, ArH ortho to cyclopentyloxy), 7.69 (1H, dd, J 8.4, 2.0 Hz, ArH para to cyclopentyloxy), and 8.51 (2H, s, pyridine $H_2$, $H_6$).

EXAMPLE 1

(E) and (Z) isomers of 1-(3-Cyclopentyloxy-4-methoxyphenyl)-2-(2,6-dichloropyrid-4-yl)ethanone oxime A mixture of Intermediate 4 (2.5 g, 6.6 mmol) and hydroxylamine hydrochloride (0.55 g, 7.9 mmol) in pyridine (15 ml) was heated to reflux for 3 days. The solvent was removed in vacuo and the residue partitioned between EtOAc (40 ml) and saturated $NaHCO_3$ solution (30 ml). The organic layer was separated, then dried ($MgSO_4$), and concentrated in vacuo. The residual brown oil was triturated with $Et_2O$ (20 ml) to afford the title compound (single isomer —(E)— or (Z)— isomer; unassigned) (1.2 g) as a white solid m.p. 139°–140° C. (Found: C, 57.60; H, 4.97; N, 6.83 $C_{19}H_{20}Cl_2N_2O_3$. requires C, 57.73; H, 5.10; N, 7.09%); $\delta_H$ ($CDCl_3$) 1.5–2.0 (8H, br m, $(CH_2)_4$), 3.81 (3H, s, OMe), 4.44 (2H, s, $CH_2$ pyridine), 4.70 (1H, br m, OCH), 6.74 (1 H, d, J 8.4Hz, ArH ortho to OMe), 6.95 (1H, d, J 2.0 Hz, ArH ortho to cyclopentyloxy), 6.97 (1 H, dd, J 8.4, 2.0 Hz, ArH para to cyclopentyloxy), 8.38 (2H, s, pyridine $H_2$, $H_6$), and 8.52 (1H, br s, NOH).

The ether soluble portion was concentrated in vacuo and triturated with hexane (20 ml) to afford (E)— and (Z)— title compound (0.53 g) as a white solid m.p. 129°–130° C. ('Hnmr indicates 1:1 mixture; $\delta_{OMe}$ 3.81 and 3.90, $\delta_{CH2}$ 4.15 and 4.44, $\delta_{OCH}$ 4.70 and 4.80, $\delta_{pyridine\ H2,\ H6}$ 8.38 and 8.48).

EXAMPLE 2

(E) and (Z) isomers of O-(Aminocarbonyl)-1-(3-cyclopentyloxy-4-methoxyphenyl)-2-(2,6-dichloropyrid-4-yl)ethanone oxime To a slowly stirred suspension of sodium cyanate (0.67 g, 10.29 mmol) in $CH_2Cl_2$ (5 ml) was added anhydrous trifiuoroacetic acid (0.587 g, 0.395 ml, 4.0 mmol) dropwise over 5 min at RT. The suspension was slowly stirred and mechanically agitated over a period of 2 h at RT, affording a gelatinous mass. A solution of the compound of Example 1 (1:1 mixture of E and Z isomers) (0.507 g, 1.3 mmol) in $CH_2Cl_2$ (2 ml) was added in one portion. The reaction mixture was stirred and agitated over 2 days then poured into saturated $NaHCO_3$ solution (25 ml) and extracted with $CH_2Cl_2$ (3×20 ml). The combined organic extract was washed with water (10 ml), dried ($Na_2SO_4$) and concentrated in vacuo. The crude product was purified by chromatography ($SiO_2$; EtOAC/hexane (1:1 )) affording the title compound (178 mg) as a mixture of E and Z isomers. Separation by HPLC ($C_{18}$ column, $CH_3CN/H_2O$(1:1) eluant, 10 ml. min⁻¹ flow rate) afforded both isomers in pure form:

Minor isomer (64 mg) as a white foam, (stereochemistry unassigned; elution time=21 min); (Found: C, 54.55; H, 4.79; N, 9.36. $C_{20}H_{21}Cl_2N_3O_4$ requires C, 54.81; H, 4.83; N, 9.59%); $\delta_H$ ($CDCl_3$) 1.5–2.0 (8H, br m, $(CH_2)_4$), 3.80 (3H, s, OMe), 4.56 (2H, s, $CH_2$ pyridine), 4.65 (1 H, br m, OCH), 5.15 (1H, br s, NH), 6.30 (1H, br s, NH), 6.74 (1H, d, J 8 Hz, ArH ortho to OMe), 6.90 (1H, d, J 2 Hz, ArH ortho to cyclopentyloxy), 7.02 (1H, dd, J 8, 2 Hz, ArH para to cyclopentyloxy), 8.45 (2H, s, pyridine $H_2$, $H_6$).

Major isomer (79 mg) as a white foam (stereochemistry unassigned; elution time=26 min); (Found: C, 54.61; H, 4.83; N, 9.53. $C_{20}H_{21}Cl_2N_3O_4$ requires C, 54.81; H, 4.83; N, 9.59%); $\delta_H$ ($CDCl_3$) 1.5–2.0 (8H, br m, $(CH_2)_4$), 3.88 (3H, s, OMe), 4.37 (2H, s, $CH_2$ pyridine), 4.78 (1H, br m, OCH), 5.0 (1H, br s, NH), 5.70 (1 H, br s, NH), 6.89 (1H, d, J 8 Hz, ArH ortho to OMe), 7.13 (1H, d, J 2 Hz, ArH Ortho to cyclopentyloxy), 7.17 (1H, dd, J 8, 2 Hz, ArH Dara to cyclopentyloxy), 8.68 (1H, br s, pyridine $H_2$, $H_6$).

EXAMPLE 3

O-Propanoyl-1-(3-cyclopentyloxy-4-methoxyphenyl)-2-(2,6-dichloropyrid-4-yl)ethanone oxime To a stirred, ice-bath cooled solution of the compound of Example 1 (0.5 g, 1.27 mmol; single isomer; stereochemistry unassigned) in $CH_2Cl_2$/pyridine (10:1, 5 ml) was added dropwise propionic anhydride (0.182 g, 0.18 ml, 1.4 mmol) under a nitrogen atmosphere. The reaction mixture was stirred briefly at this temperature then allowed to warm to RT. The solvent was removed in vacuo and the crude product azeotroped several times with toluene (3×30 ml). The obtained brown oil was subjected to chromatography ($SiO_2$, EtOAC/Hexane (1:3)) affording the title compound (0.512 g) as a white waxy solid m.p. 92°–93° C. (Found: C, 58.50; H, 5.35; N, 6.21. $C_{22}H_{24}Cl_2N_2O_4$ requires C, 58.54; H, 5.36; N, 6.21%); , $\delta_H$ ($CDCl_3$) 1.20 (3H, t, J 7.5 Hz, $CH_3CH_2$), 1.5–2.0 (8H, br m, $(CH_2)_4$), 2.41 (2H, q, J 7.5 Hz, $CH_2CH_3$), 3.82 (3H, s, OMe), 4.46 (2H, s, $CH_2$ pyridine), 4.73 (1H, br m, OCH), 6.76 (1H, d, J 8.5 Hz, ArH ortho to OMe), 7.08 (1H, d, J 2 Hz, ArH ortho to cyclopentyloxy), 7.16 (1H, dd, J 8.5, 2 Hz, ArH para to cyclopentyloxy), 8.40 (1H, s, pyridine $H_2$, $H_6$).

EXAMPLE 4

(E) and (Z) isomers of O-(Phenylcarbonyl)-1-(3-Cyclopentyloxy-4-methoxyphenyl)-2-(2,6-dichloropyrid-4-yl)ethanone oxime The compound of Example 1 (0.7 g) in dry $CH_2Cl_2$ (20 ml) was stirred and cooled in an ice-bath before adding pyridine (0.29 ml) and benzoyl chloride (0.25 ml). The reaction was stirred for 5 min under nitrogen then left to warm to RT and stir for another 4 h. The reaction mixture was partitioned between $CH_2Cl_2$ (100 ml) and saturated aqueous $NaHCO_3$ (100 ml), the phases were separated and the aqueous phase extracted with $CH_2Cl_2$ (2×50 ml). The combined organic phase was washed with brine (25 ml), dried (MgSO$_4$) and concentrated in vacuo to afford a colourless oil. Upon cooling and trituration with hexane, the title compound (0.71 g) was obtained as an off-white powder m.p. 109°–111° C. (Found C, 62.50; H, 4.85; N, 5.42. C$_{26}$H$_{24}$Cl$_2$N$_2$O$_4$ requires C, 62.53; H, 4.84; N, 5.61). δ$_H$ (CDCl$_3$) 1.5–2.0 (8H, br m, (CH$_2$)$_4$), 3.81 (3H, s, OMe), 4.61 (2H, s, pyridine), 4.73 (1H, br s OCH), 6.77 (1H, d, J 8.5 Hz, ArH ortho to methoxy), 7.10 (1H, d, J 2.2 Hz, ArH ortho to cyclopentyloxy), 7.18 (1H, dd, J 8.5, 2.2Hz, ArH para to cyclopentyloxy), 7.44–7.49 (2H, m, 2×Ph-H), 7.58–7.63 (1H, m, 1×Ph-H), 8.01 (1H, app,d, J 6 Hz, 2×Ph-H); 8.37 (2H, s, 2×pyridine H).

EXAMPLE 5

(E) and (Z) isomers of 0-Methyl-1-(3-cyclopentyloxy-4-methoxyphenyl)-2-[4-(2,6-dichloropyridine)]ethane oxime The compound of Example 1 (1.0 g) was added to a stirred suspension of NaH (0.132 g) (60% dispersion in mineral oil) in dry THF (25 ml) at RT under nitrogen. After 1 h a few crystals of tetra n-butylammonium iodide were added and the reaction stirred at RT until no more H$_2$ evolved (about 30 min). The pale yellow solution was cooled with an ice-bath before adding iodomethane. The reaction mixture was stirred for 15 min at 0° C., then 5 hr at RT, quenched with aqueous NH$_4$Cl and partitioned between 10% aqueous NH$_4$Cl (25 ml) and Et$_2$O (70 ml). The combined organic phase was washed with brine (10 ml), dried (MgSO$_4$) and concentrated in vacuo. The residual dark oil was purified by chromatography (SiO$_2$; CH$_2$Cl$_2$) to afford the title compound. (160 mg), as a mixture of 60% free base and 40% HCl salt, as a colourless oil. (Found: C, 56.72; H, 5.38; N, 6.72. C$_{20}$H$_{22}$N$_2$O$_3$Cl$_2$ (60% free base, 40% HCl salt) requires C, 56.77; H, 5.33; N, 6.62%). δ$_H$ (CDCl$_3$) 1.5–2.0 (8H, br m, (CH$_2$)$_4$), 3.80 (3H, s, ArOMe), 3.95 (3H, s, NOMe), 4.38 (2H, s, CH$_2$ pyridine), 4.70 (1H, br m, OCH), 6.73 ((1H, d, J 8.2 Hz, ArH ortho to methoxy), 6.97–7.01 (2H, m, 2×ArH), 8.39 (2H, s, 2×pyridine H).

The activity and selectivity of compounds according to the invention was demonstrated in the following tests. In these tests the abbreviation FMLP represents the peptide N-formyl-met-leu-phe.

1. Isolated Enzyme

The potency and selectivity of the compounds of the invention was determined using distinct PDE isoenzymes as follows:

i. PDE I, rabbit heart
ii. PDE II, rabbit heart
iii. PDE III, rabbit heart, Jurkat cells
iv. PDE IV, HL60 cells, rabbit brain, rabbit kidney and human recombinant PDE IV
v. PDE V, rabbit lung, guinea pig lung A gene encoding human PDE IV has been cloned from human monocytes (Livi, et al., 1990, *Molecular and Cellular Biology*, 10. 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (Beavo and Reifsnyder, 1990, *TIPS*, 11. 150). These recombinant enzymes, particularly the human eosinophil recombinant PDE IV, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 μl of standard mixture containing (final concentrations): 50 mM 2-[[tris (hydroxymethyl)methyl]amino]-1-ethanesulphonic acid (TES) —NaOH buffer (pH 7.5), 10 mM MgCl$_2$, 0.1 μM [$^3$H]-cAMP and vehicle or various concentrations of the test compounds. The reaction was initiated by addition of enzyme and conducted at 30° C. for between 5 to 30 min. The reaction was terminated by addition of 50 μl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES—NaOH buffer (pH8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction.

Compounds according to the invention cause a concentration-dependent inhibition of recombinant PDE IV at 0.1–1000 nM with little or no activity against PDE I, II, III or V at concentrations up to 100 μM.

2. The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intraperitoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

3. Suppression of Leukocyte Function

Compounds of the invention were investigated for their effects on superoxide generation, chemotaxis and adhesion of neutrophils and eosinophils. Isolated leukocytes were incubated with dihydrocytochalasin B for superoxide generation only and test compound prior to stimulation with FMLP. The most potent compounds of the Examples caused a concentration-dependent inhibition of superoxide generation, cherootaxis and adhesion at concentrations of 0.1 nM to 1 μM.

Lipopolysaccharide (LPS)-induced synthesis of tumour necrosis factor (TNF) by human peripheral blood monocytes (PBM) is inhibited by compounds of the invention at concentrations of 0.01 nM to 10 μM.

4. Adverse Effects

In general, in our tests, compounds of the invention have had no observed toxic effects when administered to animals at pharmacologically effective doses.

We claim:
1. A compound of formula (1)

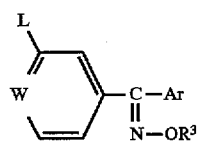

wherein

=W— is =C(Y)—, where Y is halogen or an alkyl or —XR" group, X is —O—, —S(O)$_m$—, or —N(R$^b$)—, R$^a$ is hydrogen or an optionally substituted alkyl group, R$^b$ is hydrogen or an optionally substituted alkyl group, and m is zero or an integer of 1 or 2;

L is an —XR, —C(R$^5$)=C(R$^1$)(R$^2$) or —(CHR$^5$)$_n$CH(R$^1$)(R$^2$) group where n is zero or the integer 1, R is an optionally substituted alkyl, alkenyl, cycloalkyl or cyloalkenyl group, R$^5$ is hydrogen, fluorine or a methyl group, and R$^1$ and R$^2$, which may be the same or different, are each hydrogen, fluorine, —CN, —NO$_2$ or an optionally substituted alkyl, alkenyl, alkynyl, alkoxy, alkylthio, —CO$_2$R$^6$, —CONR$^7$R$^8$ or —CSNR$^7$R$^8$ group, where R$^6$, R$^7$ and R$^8$, which may be the same or different, are each hydrogen or an optionally substituted alkyl, aralkyl or aryl group, or R$^1$ and R$^2$, together with the carbon atom to which they are attached, are linked to form an optionally substituted cycloalkyl or cycloalkenyl group;

Ar is a —(CH$_2$)$_n$—Z—Ar' group, where Ar' is an optionally substituted monocyclic or bicyclic heteroaryl group, Z is a bond, —O—, —S— or —N(R$^b$)—, and n is zero or the integer 1, 2, 3 or 4; and R$^3$ is hydrogen or an optionally substituted alkyl, alkenyl, alkynyl, —C(O)R$^4$ or —C(S)R$^4$ group, where R$^4$ is an amino, alkylamino, arylamino, alkoxy, aryloxy or an optionally substituted alkyl group;

and the salts, solvates, hydrates, prodrugs and N-oxides thereof.

2. A compound according to claim 1 wherein =W— is =C(Y)— in which Y is a —XR$^a$ group, and L is a —XR group.

3. A compound according to claim 2 wherein —X— is —O—, R$^a$ is a C$_{1-3}$alkyl group and R is an optionally substituted cyclopentyl group.

4. A compound according to claim 2 wherein Ar is a group —CH$_2$—Ar'.

5. A compound according to claim 4 wherein Ar' is an optionally substituted pyridyl group.

6. A compound according to claim 5 wherein R$^3$ is a hydrogen atom or a —CONH$_2$, or —COR$^7$ group where R$^7$ is an optionally substituted alkyl or phenyl group.

7. A compound which is the (E) and/or (Z) isomer of:
1-(3-cyclopentyloxy-4-methoxyphenyl)-2-(2,6-dichloro-4-pyridyl) ethanone oxime;
O-(aminocarbonyl)-1-(3-cyclopentyloxy-4-methoxy-phenyl)-2-(2,6-dichloro-pyrid-4-yl)ethanone oxime;
O-propanoyl-1-(3-cyclopentyloxy-4-methoxy-phenyl)-2-(2,6-dichloropyrid-4-yl)ethanone oxime;
O-benzoyl-2-(2,6-dichloropyridyl)-1-(3-cyclopentyl-oxy-4-methoxyphenyl)-ethanone oxime;
O-methyl-1-(3-cyclopentyloxy-4-methoxyphenyl)-2-[4-(2,6-dichloropyridine)]ethanone oxime;
and the salts, solvates, hydrates, prodrugs and N-oxides thereof.

8. A compound according to claim 7 which is O-(aminocarbonyl)-1-(3-cyclopentyloxy-4-methoxyphenyl)-2-(2,6-dichloropyrid-4-yl)ethanone oxime; or a salt, solvate, hydrate or N-oxide thereof.

9. A compound according to claim 8 which is the (E) isomer.

10. A compound according to claim 9 which is the (Z) isomer.

11. A pharmaceutical composition which comprises a compound of formula (1)

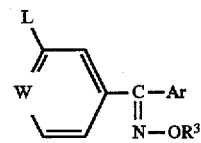

wherein

=W— is =C(Y)—, where Y is halogen or an alkyl or —XR$^a$ group, X is —O—, —S(O)$_m$—, or —N(R$^b$)—, R$^a$ is hydrogen or an optionally substituted alkyl group, R$^b$ is hydrogen or an optionally substituted alkyl group, and m is zero or an integer of 1 or 2;

L is an —XR, —C(R$^5$)=C(R$^1$)(R$^2$) or —(CHR$^5$)$_n$CH(R$^1$)(R$^2$) group where n is zero or the integer 1, R is an optionally substituted alkyl, alkenyl, cycloalkyl or cyloalkenyl group, R$^5$ is hydrogen, fluorine or a methyl group, and R$^1$ and R$^2$, which may be the same or different, are each hydrogen, fluorine, —CN, —NO$_2$ or an optionally substituted alkyl, alkenyl, alkynyl, alkoxy, alkylthio, —CO$_2$R$^6$, —CONR$^7$R$^8$ or —CSNR$^7$R$^8$ group, where R$^6$, R$^7$ and R$^8$, which may be the same or different, are each hydrogen or an optionally substituted alkyl, aralkyl or aryl group, or R$^1$ and R$^2$, together with the carbon atom to which they are attached, are linked to form an optionally substituted cycloalkyl or cycloalkenyl group;

Ar is a —(CH$_2$)$_n$—Z—Ar' group, where Ar' is an optionally substituted monocyclic or bicyclic heteroaryl group, Z is a bond, —O—, —S— or —N(R$^b$)—, and n is zero or the integer 1, 2, 3 or 4; and R$^3$ is hydrogen or an optionally substituted alkyl, alkenyl, alkynyl, —C(O)R$^4$ or —C(S)R$^4$ group, where R$^4$ is an amino, alkylamino, arylamino, alkoxy, aryloxy or an optionally substituted alkyl group; and the salts, solvates, hydrates, prodrugs and N-oxides thereof;

together with one or more pharmaceutically acceptable carriers excipients or diluents.

12. A pharmaceutical composition comprising, in combination with one or more pharmaceutically acceptable carriers, excipients or diluents, O-(aminocarbonyl)-1-(3-cyclopentyloxy-4-methoxyphenyl)-2-(2,6-dichloropyrid-4-yl)ethanone oxime, or a salt, solvate, hydrate or N-oxide thereof.

13. A composition according to claim 12 which comprises (E)—O—(aminocarbonyl)-1-(3-cyclopentyloxy-4-methoxyphenyl)-2-(2,6-dichloropyrid-4-yl)ethanone oxime; or a salt, solvate, hydrate or N-oxide thereof.

14. A composition according to claim 12 which comprises (Z)—O—(aminocarbonyl)-1-(3-cyclopentyloxy-4-methoxyphenyl)-2-(2,6-dichloropyrid-4-yl)ethanone oxime; or a salt, solvate, hydrate or N-oxide thereof.

15. A method of preventing or treating an inflammatory disease in a patient comprising administering to the patient, in an amount effective to elevate intracellular levels of adenosine 3',5'-cyclic monophosphate (cAMP), a composition which comprises a selective inhibitor of a phosphodiesterase (PDE) IV isoenzyme selected from a compound according to claim 1 and a pharmaceutically acceptable carrier, excipient or diluent.

16. A method according to claim 1 wherein said inflammatory disease is asthma.

17. A method according to claim 15 wherein said inflammatory disease is selected from the group consisting of inflammatory airway disease, chronic bronchitis, eosinophilic granuloma, cellular proliferative disorders, endotoxic shock, septic shock, ulcerative colitis, Crohn's disease, reperfusion injuries, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

18. A process for the preparation of a compound of formula (1)

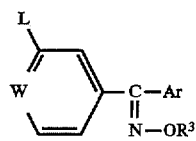
(1)

wherein

=W— is =C(Y)—, where Y is halogen or an alkyl or —XR$^a$ group, X is —O—, —S(O)$_m$—, or —N(R$^b$)—, R$^a$ is hydrogen or an optionally substituted alkyl group, R$^b$ is hydrogen or an optionally substituted alkyl group, and m is zero or an integer of 1 or 2;

L is an —XR, —C(R$^5$)=C(R$^1$)(R$^2$) or —(CHR$^5$)$_n$CH(R$^1$)(R$^2$) group where n is zero or the integer 1, R is an optionally substituted alkyl, alkenyl, cycloalkyl or cyloalkenyl group, R$^5$ is hydrogen, fluorine or a methyl group, and R$^1$ and R$^2$, which may be the same or different, are each hydrogen, fluorine, —CN, —NO$_2$ or an optionally substituted alkyl, alkenyl, alkynyl, alkoxy, alkylthio, —CO$_2$R$^6$, —CONR$^7$R$^8$ or —CSNR$^7$R$^8$ group, where R$^6$, R$^7$ and R$^8$, which may be the same or different, are each hydrogen or an optionally substituted alkyl, aralkyl or aryl group, or R$^1$ and R$^2$, together with the carbon atom to which they are attached, are linked to form an optionally substituted cycloalkyl or cycloalkenyl group;

Ar is a —(CH$_2$)$_n$—Z—Ar' group, where Ar' is an optionally substituted monocyclic or bicyclic heteroaryl group, Z is a bond, —O—, —S— or —N(R$^b$)—, and n is zero or the integer 1, 2, 3 or 4; and R$^3$ is hydrogen or an optionally substituted alkyl, alkenyl, alkynyl, —C(O)R$^4$ or —C(S)R$^4$ group, where R$^4$ is an amino, alkylamino, arylamino, alkoxy, aryloxy or an optionally substituted alkyl group; and the salts, solvates, hydrates, prodrugs and N-oxides thereof; which comprises in a final step (a) reacting a compound of formula (3)

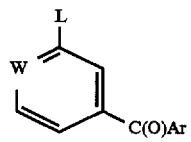
(3)

with a hydroxylamine NH$_2$OR$^3$ or a salt thereof;

(b) alkylating an intermediate of formula (10)

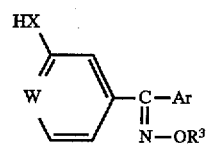
(10)

where X is —O—, —S— or —N(R$^b$)—, with a reagent RL$^1$, where L$^1$ is a leaving group;

(c) coupling a compound of formula (12)

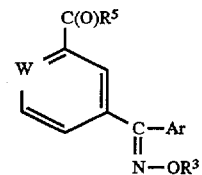
(12)

where R$^5$ is hydrogen or a methyl group, with an olefination agent to yield a compound of formula (1), where L is —C(R$^5$)=C(R$^1$)(R$^2$) group;

(d) reacting a compound of formula (12)

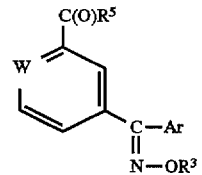
(12)

where R$^5$ is hydrogen or a methyl group, with an organometallic reagent followed by dehydration of the resulting alcohol to give a compound of formula (1), where L is a —C(R$^5$)=C(R$^1$) group in which R$^1$ is an optionally substituted alkyl, alkenyl or alkynyl group;

(e) reacting a compound of formula (10)

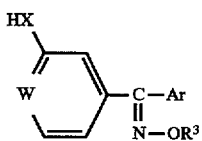
(10)

wherein —X— is —O—, with (1) a triflate reagent followed by (2) an organostannate to give a compound of formula (1), wherein L is a —C(R$^5$)=C(R$^1$)(R$^2$) or —(CHR$^5$)$_n$CHR$^1$R$^2$ group; or (f) interconverting a compound of formula (1) to another compound of formula (1).

* * * * *

UNITED STATES PATENT AND TRADEMARK OFFICE
CERTIFICATE OF CORRECTION

PATENT NO. : 5,693,659
DATED : December 2, 1997
INVENTOR(S) : Head et al.

It is certified that error appears in the above-indentified patent and that said Letters Patent is hereby corrected as shown below:

Column 1, line 4, delete "relatss" and insert --relates-- therefor.

Column 1, line 19, delete "Which" and insert --which-- therefor.

Column 1, line 24, delete "etal" and insert --et al-- therefor.

Column 1, line 31, delete "effectis" and insert --effects-- therefor.

Column 2, line 21, delete "solyates" and insert --solvates-- therefor.

Column 2, line 41, delete "=C(NHC$_3$)-" and insert --=C(NHCH$_3$)--- therefor.

Column 4, line 13, delete "-C(S)OR7" and insert ---C(S)OR$^7$-- therefor.

Column 5, line 13, delete "-CONHAlk$_2$" and insert ---CONHAlk$^2$-- therefor.

Column 5, line 38, after "-Alk$^2$(R$^{10}$)$_m$", insert --m--.

Column 6, line 41, delete "diethylaminosuiphonyl" and insert --diethylaminosulphonyl-- therefor.

Column 7, line 1, delete "aminothiocarbonyiamino" and insert --aminothiocarbonylamino-- therefor.

Column 7, line 16, delete "acylaminosuiphonylamino" and insert --acylaminosulphonylamino-- therefor.

UNITED STATES PATENT AND TRADEMARK OFFICE
CERTIFICATE OF CORRECTION

PATENT NO. : 5,693,659
DATED : December 2, 1997
INVENTOR(S) : Head et al.

It is certified that error appears in the above-indentified patent and that said Letters Patent is hereby corrected as shown below:

Column 7, line 55, delete "pipeddine" and insert --piperidine-- therefor.

Column 9, line 56, delete "turnour" and insert --tumour-- therefor.

Column 10, line 46, delete "properlant" and insert --propellant-- therefor.

Column 14, line 15, delete "aidehyde" and insert --aldehyde-- therefor.

Column 14, line 60, delete "trifiuoromethanesulphonic" and insert --trifluoromethanesulphonic-- therefor.

Column 15, lines 7 to 8, delete "reaotion" and insert --reaction-- therefor.

Column 16, line 40, delete "Et2O" and insert --$Et_2O$-- therefor.

UNITED STATES PATENT AND TRADEMARK OFFICE
CERTIFICATE OF CORRECTION

PATENT NO. : 5,693,659
DATED : December 2, 1997
INVENTOR(S) : Head et al.

It is certified that error appears in the above-indentified patent and that said Letters Patent is hereby corrected as shown below:

Column 16, line 49, delete "comDound" and insert --compound-- therefor.

Column 18, line 26, delete "Dara" and insert --para-- therefor.

Column 19, line 20, delete "Nail" and insert --NaH-- therefor.

Column 20, line 56, delete "cherootaxis" and insert --chemotaxis-- therefor.

Column 21, line 12, claim 1, delete "-XR"" and insert ---XR$^a$-- therefor.

Signed and Sealed this

Twentieth Day of July, 1999

*Attest:*

Q. TODD DICKINSON

*Attesting Officer*   *Acting Commissioner of Patents and Trademarks*